United States Patent [19]

Lovgren et al.

[11] Patent Number: 4,886,506
[45] Date of Patent: Dec. 12, 1989

[54] SOFT TIP CATHETER

[75] Inventors: Eric M. Lovgren, Dana Point; Abdul-Kader A. El-Tibi, Costa Mesa, both of Calif.

[73] Assignee: Baxter Travenol Laboratories, Inc., Deerfield, Ill.

[21] Appl. No.: 271,351

[22] Filed: Nov. 10, 1988

Related U.S. Application Data

[63] Continuation of Ser. No. 946,491, Dec. 23, 1986, abandoned.

[51] Int. Cl.$^4$ .............................................. A61M 25/00
[52] U.S. Cl. ..................................... 604/280; 604/96; 604/282; 128/658
[58] Field of Search ............................. 604/280–284; 128/656–658

[56] References Cited

U.S. PATENT DOCUMENTS

| | | | |
|---|---|---|---|
| 3,498,286 | 9/1966 | Polanyi | 604/282 |
| 3,598,126 | 8/1971 | Hoeltzebein | 604/282 |
| 3,618,614 | 11/1971 | Flynn | 128/658 |
| 4,044,765 | 8/1977 | Kline | 604/282 |
| 4,238,447 | 8/1981 | Flynn | 428/36 |
| 4,385,635 | 5/1983 | Ruiz | 604/280 |
| 4,419,095 | 12/1983 | Nebergall et al. | 604/96 |
| 4,425,919 | 1/1984 | Alston, Jr. et al. | 604/282 |
| 4,531,943 | 7/1985 | Van Tassel et al. | 128/658 |
| 4,551,292 | 11/1985 | Fletcher et al. | 128/658 |
| 4,563,181 | 1/1986 | Wijayarathna et al. | 604/280 |
| 4,574,173 | 3/1986 | Bennett | 604/280 |
| 4,577,543 | 3/1986 | Wilson | 87/11 |
| 4,596,563 | 6/1986 | Pande | 604/282 |
| 4,636,346 | 1/1987 | Gold et al. | 604/280 |
| 4,639,252 | 1/1987 | Kelly et al. | 604/282 |

Primary Examiner—Stephen C. Pellegrino
Attorney, Agent, or Firm—Gordon L. Peterson

[57] ABSTRACT

A catheter includes a catheter tube extending to a distal end portion that terminates at a terminal end of the catheter tube, the distal end portion including a tapered portion extending between the terminal end and a transition region on the distal end portion set back slightly from the terminal end. The tapered portion has a cross sectional area that decreases toward the terminal end to define a frustoconically-shaped outer surface extending from the transition region to the terminal end on which a soft tip member is mounted. The tip member has a size and shape adapted to be placed over the tapered portion coaxially, and a composition softer than that of the distal end portion that is suitable for bonding to the frustoconically-shaped outer surface.

23 Claims, 1 Drawing Sheet

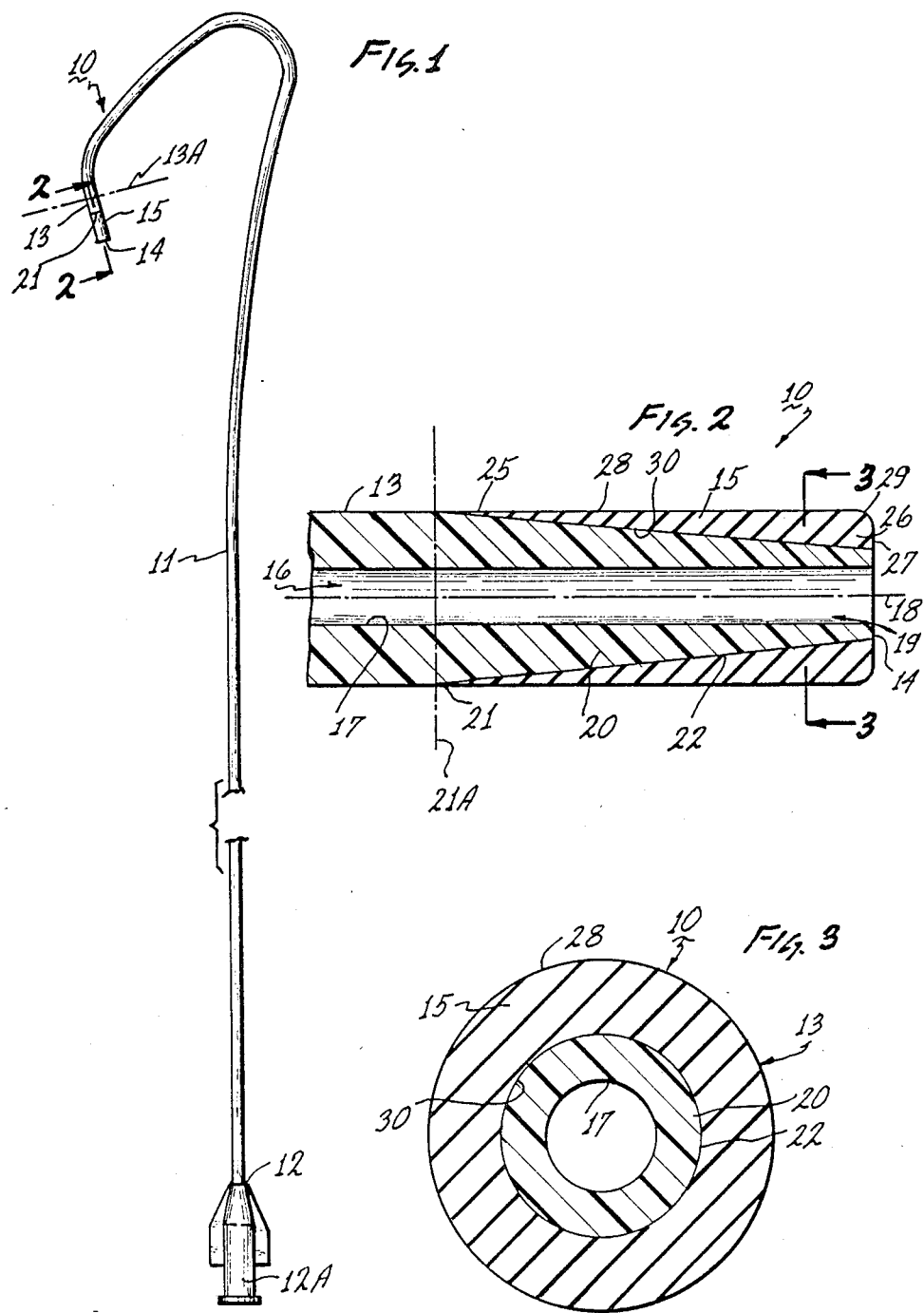

SOFT TIP CATHETER

This application is a continuation of Application Ser. No. 946,491 filed Dec. 23, 1986 now abandoned and also entitled "Soft Tip Catheter".

BACKGROUND OF THE INVENTION

1. Technical Field. This invention relates generally to catheters adapted to be introduced into a living body, and more particularly to a catheter featuring a new and improved soft tip construction.

2. Background Information. Soft tip catheters, such as coronary angiography and guiding catheters, often employ a soft tip as a precautionary measure. Intended for less invasive vascular procedures, these catheters include the soft tip to avoid injury to vulnerable vessels and arteries. In addition, the soft tip reduces trauma in certain guiding catheter procedures that lodge the catheter tip in the coronary ostium. Thus, the soft tip aspect of catheter design is of recognized significance and each detail of soft tip construction of corresponding importance.

Apart from the soft tip, however, the catheter must exhibit other important attributes. One of these is commonly referred to as torque control, i.e., the ability to transmit a twisting force along its length. Sufficient torque control enables carefully controlled maneuvering of the catheter by the application of twisting forces at the proximal end of the catheter that are transmitted along the catheter axis towards the distal end. However, the features of existing catheter designs that provide greater torque control often complicate addition of a soft tip.

For example, U.S. Pat. No. 4,385,635 to Ruiz describes a catheter composed of a urethane jacketed polyamide tube that provides a degree of reinforcement to the catheter tube for better torque control. However, the soft tip is provided by forming it from the outer layer, and the manner in which the inner layer tapers to zero at a point set back from the distal end results in a discontinuity in the coefficient of friction along the tube interior. This interferes with advancement of another device, such as a probe or inner catheter, within the catheter tube.

U.S. Pat. No. 4,238,447 to Flynn describes another integrally formed soft tip construction employing a multilayered catheter tube. Unlike the Ruiz design, the inner surface of the catheter tube extends fully to the distal end to avoid any abrupt change in coefficient of friction. However, the cross section of the inner and outer layers vary over the length of the catheter tube, and it otherwise suffers from the inconvenience and expense of fabrication common to integral designs. This common concern results, in part, from the need to form the tip with the catheter tube. Thus, it is not possible to cut a selected length from preformed tubing stock and then supply the desired soft tip.

U.S. Pat. No. 4,563,181 to Wijayarathna overcomes some of these problems with a soft catheter tip butt-fused in end-to-end relationship to a nylon catheter tube body, non-reinforced monotubular structures having a difference in Shore A hardness greater than 10 being used in both the tip and body portions. Although providing a soft tip without integral construction, this arrangement results in an abrupt interface between tip and body that often incurs stresses in use that buckle the catheter at the interface or cause the tip to break off. Thus, the tip may break off during deep engagement with severe consequences to the patient.

Despite the use of a lap joint for attaching the soft tip described in U.S. Pat. No. 4,531,943 to Van Tassel, this design is also vulnerable to tip breakage along the portion of the joint disposed generally perpendicular to the catheter tube axis. As in the Wijayarathna et al. construction, external forces applied against the tip perpendicular to the catheter tube axis tend to pull the tip apart from the body along the perpendicularly disposed portion of the joint. In addition, the abrupt changes in cross section result in stress concentrations. When these forces overcome the bond, the tip breaks off.

The perpendicularly disposed joint also frustrates use of a multilayered catheter tube body for better torque control. It does so because the layers of a multilayered catheter tube present, in cross section, small, dissimilar areas to which to bond the tip, and this compounds the difficulty of providing a strong bond to each layer that has sufficient surface area to withstand the external forces applied. Thus, existing soft tip designs using a separate tip often employ catheter tubes to which the tip can be bonded advantageously, but these often exhibit softness in the warmth of the body interior that actually reduces torque control.

Therefore, it is desirable to have a new and improved soft tip catheter that overcomes these concerns--one employing a catheter tube exhibiting better torque control that includes a separate soft tip attached to the catheter tube with a better joint in a manner enabling more convenient and less expensive fabrication.

SUMMARY OF THE INVENTION

This invention recognizes the problems associated with the prior art and provides a new and improved soft tip catheter with the desired attributes.

Briefly, the above-mentioned and further objects of the present invention are realized by providing a catheter body or tube having desired torque control attributes to which is attached a soft tip of superior design with a joint less prone to break.

The catheter tube may be of a multilayered design for reinforced torque control, and it has a distal end portion extending to a distal or terminal end of the catheter tube. A tapered portion of the distal end portion extends between the terminal end and a transition region. The transition region is nearer the distal end than the proximal end of the catheter tube, and is preferably on the distal end portion set back slightly from the terminal end. The the tapered portion has a cross sectional area that decreases toward the terminal end to thereby eliminate abrupt changes in cross section that would tend to produce stress concentrations and a corresponding likelihood of buckling.

A tip member is attached to the tapered portion. The tip member has a size and shape adapted to be placed over the tapered portion and is softer than the distal end portion. The tip member preferably has a composition that is suitable for bonding to the tapered portion. In one form of the invention, the tapered portion defines a frustoconically-shaped surface to which the tip is fused by RF welding. This results in a non-perpendicularly disposed joint of greater surface area, and external forces applied perpendicularly tend more to force the tip against the tube than pull the two apart. Also, the tip member is generally coterminus with the tapered portion so that no discontinuity in coefficient of friction is presented. More specifically, a probe or inner catheter advanced within the catheter tube does not contact the softer tip.

Thus, the device of this invention overcomes many drawbacks of existing soft tip catheters. It enables use of a reinforced catheter tube for greater torque control by providing a tip that is bonded along a tapered surface, and in this regard the tapered portion preferably begins distally of the distal end of the reinforced portion of the catheter tube with the tapered portion and soft tip being coterminus. The resulting joint extends longitudinally along the tapered portion so that it covers a greater area. In addition, the joint is not disposed perpendicularly to the catheter tube axis so that it is less prone to fail under stress. Moreover, the soft tip catheter is conveniently and inexpensively manufactured using a selected length of catheter tubing stock.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a plan view of an angiography catheter constructed according to the invention;

FIG. 2 is an enlarged longitudinal cross section of the distal end portion of the catheter tube taken on line 2—2 of FIG. 1; and FIG. 3 is a further enlarged transverse cross section of the distal end portion taken on line 3—3 of FIG. 2.

DESCRIPTION OF THE PREFERRED EMBODIMENTS

Referring now to the drawings, and particularly to FIG. 1, there is shown a new and improved soft tip catheter 10 constructed according to the invention. Although the catheter 10 is designed for use as a one hundred centimeter long angiography catheter with a Judkins curve and 8 French tip, the inventive concepts disclosed are equally applicable to any of various other catheters adapted to be introduced into a living body.

Generally, the catheter 10 includes a catheter body or tube 11, illustrated foreshortened for convenience, that extends from a proximal end portion 12 at or within a proximal fitting 12A to a distal end portion 13 terminating at a distal or terminal end 14. A soft tip member or tip 15 is included attached to the catheter tube 11 at the distal end portion 13, and this inhibits damage to arteries and vessels when the catheter 10 is introduced into the vascular system according to known surgical procedures.

Considering first the catheter tube 11, it is preferably a reinforced tubular structure exhibiting desired torque control characteristics, and it has a size and shape adapted to be used as an angiography catheter to be introduced into the coronary ostium. It may be of multilayer construction similar to the construction described in U.S. Pat. No. 4,577,543 to Wilson, but the inventive aspects of the soft tip design to be subsequently discussed are equally applicable to a nonreinforced catheter tube of single layer construction. In this regard, the reinforcing preferably terminates proximally of the tip 15, such as in the general region of intersection of the catheter tube 11 and the plane designated reference numeral 13A in FIG. 1.

The illustrated catheter tube 11 defines a lumen 16 bounded by inner surface 17 that extends substantially throughout the length of the catheter tube 11 along a catheter tube axis 18 to an opening 19 at the terminal end 14 (FIG. 2), and it may have other lumens (not shown). The lumen 16 may vary in size throughout the length of the catheter tube 11, the illustrated lumen 16 decreasing from 9 French at the proximal end 12 to 8 French at the distal end portion, i.e., an inner diameter at the terminal end 14 of approximately 0.074 inches (1.88 millimeters).

The catheter tube 11 is at least partially composed of a suitable material exhibiting desired torque control characteristics, such as a polyether-polyamide material or a polyether block amide (PEBA) utilizing Nylon 12. In this regard, the illustrated embodiment employs a PEBA material sold under the designation PEBAX 6333SA. This material has a Shore 63 hardness, and it does not go soft when subjected to typical body temperatures. Thus, it retains its ability to transmit twisting forces along its length.

The distal end portion 13 includes a tapered portion 20 extending from the terminal end 14 to a transition region 21 set back from the terminal end 14. The transition region 21 is in the general region of the intersection of the catheter tube 11 and the plane designated reference numeral 21A in FIG. 2, and the tapered portion 20 has a cross sectional area that decreases from the transition region 21 toward the terminal end 14. It decrease in cross sectional area to define a frustoconically-shaped outer surface 22 having an outside diameter that decreases from approximately 0.104 inches (2.64 millimeters) at the transition region 21 (8 French) to a value slightly greater than the inner diameter of the lumen 16 at the terminal end 14 (0.03 to 0.3 millimeters). These values may vary according to the specific catheter design constructed.

The transition region 21 is set back from the terminal end 14 a distance such that the frustoconically-shaped outer surface 22 has sufficient surface area to which to bond the tip 15. However, it is not set back far enough to fall within a portion of the catheter tube 11 typically subjected to stress, such as the curved regions of the Judkins curve in the illustrated embodiment. Thus, the transition region 21 may be set back a distance on the order of one to ten millimeters.

The tip 15 is composed of a softer material than the distal end portion 13 of the catheter tube 11, such as a polyether-polyamide material or a PEBA material sold under the designation PEBAX 2533SA. This material has a Shore 25 hardness that protects against damage to arteries and vessels when the catheter 10 is in use. It is preferably imperforate, and it is bonded to the frustoconically-shaped outer surface 22 by suitable means such as RF welding.

The tip 15 has a size and shape adapted to be placed over the tapered portion coaxially. It may have any of various exterior forms, the illustrated tip 15 having a rearward portion 25 with an outside diameter generally conforming to the outside diameter of the distal end portion 13 at the transition region 21, and a forward portion 26 extending to a terminal end 27 of the tip 15 that is generally coterminus with the terminal end 14 of the catheter tube 11. Thus, the contour of the tip 15 blends smoothly into the contour of the distal end portion 13 at the transistion region 21.

The tip 15 defines a cylindrically-shaped outer surface 28 that extends from the rearward portion 25 to a rounded portion 29 of the forward portion 27, the rounded portion 29 providing transition to the terminal end 27 of the tip 15 that further reduces trauma during catheter use. The tip 15 also defines a circularly-shaped inner surface 30 extending from the transition region 21 to the terminal end 27 of the tip 15. The inner surface 30 has a size and shape adapted to mate with the outer surface 22 of the tapered portion 20, and when these surfaces are bonded together a superior soft tip construction results.

Although an exemplary embodiment of the invention has been shown and described, many changes, modifications, and substitutions may be made by one having ordinary skill in the art without necessarily departing from the spirit and scope of this invention.

What is claimed is:

1. A catheter comprising:
   an elongated, flexible catheter body having a proximal end, a distal end, at least one lumen, and a distal end portion extending to the distal end of the catheter body;
   the distal end portion being tapered and terminating proximally at a transition region which is nearer the distal end than the proximal end of the catheter body, the distal end portion having a cross sectional area that decreases toward the distal end; and
   a a biocompatible tip member attached to the distal end portion and being softer than the distal end portion, said tip member terminating substantially at the distal end of the catheter body.

2. A catheter as recited in claim 1, wherein:
   the distal end portion has a frustoconically-shaped outer surface extending from the transition region distally; and
   the tip member has an inner surface that generally matches the outer surface of the distal end portion.

3. A catheter as recited in claim 2, wherein the tip member includes:
   a proximal portion extending to the transition region, the proximal portion having an outer surface that closely matches the outer surface of the catheter body at the transition region.

4. A catheter as recited in claim 1, wherein:
   the distal end of the tip member is a rounded.

5. A catheter as recited in claim 1, wherein:
   the tip member has a circularly-shaped cross section of generally uniform outside diameter throughout the length of the tip member.

6. A catheter as recited in claim 1, wherein:
   the distal end portion has an outside and an inside diameter at the distal end of the catheter tube; and
   the outside diameter is greater than the inside diameter by approximately 0.03 to 0.3 millimeters.

7. A catheter as recited in claim 1, wherein:
   the transition region is set back from the distal end a distance of approximately 1 to 10 millimeters.

8. A catheter as recited in claim 1, wherein:
   the distal end portion of the catheter body is at least partially composed of a polyether-polyamide material.

9. A catheter as recited in claim 1, wherein:
   the tip member is at least partially composed of a polyether-polyamide material.

10. A catheter as recited in claim 1, wherein:
    the tip member is fused to the tapered portion.

11. A catheter as recited in claim 10, wherein:
    the tip member is fused to the tapered portion by RF welding.

12. A catheter, comprising:
    a catheter tube having a longitudinal axis, a distal end portion, and a terminal end to which the distal end portion extends, the distal end portion having a specified inner diameter at the terminal end and a specified outer diameter at a transition region on the distal end portion that is set back a specified distance from the terminal end which is less than the full length of the catheter tube;
    a tapered portion of the distal end portion defining a frustoconically-shaped outer surface extending from the transition region to the terminal end, the tapered portion having a circularly-shaped cross sectional area generally perpendicular to the longitudinal axis the outer diameter of which decreases from the transition region toward the terminal end to a size at the terminal end that is greater than the inner diameter of the distal end portion by a specified amount; and
    a tip member composed of material softer than the material of which the distal end portion is composed that has a size and shape disposed about a tip member axis that is adapted to be placed over the tapered portion coaxially and attached to the frustoconically-shaped outer surface, the tip member having a length extending along the tip member axis that is generally equal to the specified distance that the transition region is set back from the terminal end, and a circularly-shaped cross sectional area generally perpendicular to the tip member axis the outer diameter of which is generally equal to the specified outer diameter of the distal end portion at the transition region, and the inner diameter of which generally matches the outer diameter of the tapered portion.

13. A catheter as recited in claim 12, wherein:
    the transition region is set back a distance of approximately one to ten millimeters from the terminal end of the catheter tube.

14. A catheter as recited in claim 12, wherein:
    the outer diameter of the distal end portion at the terminal is greater than the inner diameter of the distal end portion by an amount of 0.03 to 0.3 millimeters.

15. A catheter as recited in claim 12, wherein:
    the distal end portion of the catheter tube is at least partially composed of a polyether-polyamide material.

16. A catheter as recited in claim 12, wherein:
    the tip member is at least partially composed of a polyether-polyamide material.

17. A catheter as recited in claim 12, wherein:
    the tip member is fused to the tapered portion.

18. A catheter as recited in claim 17, wherein:
    the tip member is fused to the tapered portion by RF welding.

19. A catheter comprising:
    a multilayer catheter tube having a transition region, a proximal end, and a distal end, the transition region being closer to the distal end than the proximal end, the catheter tube having a distal end portion extending to the distal end of the catheter tube, and reinforcement which terminates proximally of the transition region;
    the distal end portion having a tapered portion extending from the distal end to the transition region of the catheter tube, the tapered portion having a cross sectional area that decreases toward the distal end; and a tip member attached to the tapered portion, the tip member having a size and shape adapted to be placed over the tapered portion and being softer than the distal end portion.

20. A catheter as recited in claim 19 wherein the tip member terminates proximally at the transition region and distally substantially at the distal end of the catheter.

21. A catheter as recited in claim 20 wherein the contour of the tip member blends smoothly into the contour of the catheter body at the transition region.

22. A catheter comprising:
a catheter tube having a distal end portion extending to a terminal end of the catheter body;
the distal end portion having a tapered portion which extends from the terminal end to a transition region on the distal end portion, the transition region being set back slightly from the terminal end, the tapered portion having a cross sectional area that decreases toward the terminal end; and
a tip member attached to the tapered portion, the tip member having a size and shape adapted to be placed over the tapered portion coaxially and a composition softer than that of the distal end portion that is suitable for bonding to the tapered portion, said tip member terminating proximally substantially at the transition region and distally substantially at the terminal end.

23. A catheter as recited in claim 22 wherein the contour of the tip member blends smoothly into the contour of the catheter body at the transition region.

* * * * *